(12) United States Patent
Sharp et al.

(10) Patent No.: US 6,183,464 B1
(45) Date of Patent: Feb. 6, 2001

(54) SAFETY SYRINGE WITH RETRACTABLE NEEDLE AND UNIVERSAL LUER COUPLING

(75) Inventors: Fraser R. Sharp; Donald A. McLean, both of Vancouver (CA)

(73) Assignee: Inviro Medical Devices Ltd., Bridgetown (KN)

( * ) Notice: Under 35 U.S.C. 154(b), the term of this patent shall be extended for 0 days.

(21) Appl. No.: 09/087,953

(22) Filed: Jun. 1, 1998

(51) Int. Cl.⁷ .................................................. A61M 25/16

(52) U.S. Cl. ......................... 604/533; 604/195; 604/240

(58) Field of Search .................................. 604/187, 195, 604/240, 241, 533, 110

(56) References Cited

U.S. PATENT DOCUMENTS

| | | |
|---|---|---|
| 2,688,325 | 9/1954 | Lockhart . |
| 2,722,215 | 11/1955 | Dahlgren . |
| 2,880,725 | 4/1959 | Kendall . |
| 2,888,923 | 6/1959 | Reis . |
| 3,301,256 * | 1/1967 | Cowley . |
| 3,306,290 | 2/1967 | Weltman . |
| 3,354,882 | 11/1967 | Coanda . |
| 3,356,089 | 12/1967 | Francis . |
| 3,487,834 | 1/1970 | Smith, Jr. et al. . |
| 3,527,216 | 9/1970 | Snyder . |
| 3,828,775 | 8/1974 | Armel . |
| 3,884,230 | 5/1975 | Wulff . |
| 3,930,492 | 1/1976 | Hatsuno et al. . |
| 4,026,287 | 5/1977 | Haller . |
| 4,085,737 | 4/1978 | Bordow . |
| 4,139,009 | 2/1979 | Alvarez . |
| 4,258,713 | 3/1981 | Wardlaw . |
| 4,266,543 | 5/1981 | Blum . |
| 4,266,544 | 5/1981 | Wardlaw . |
| 4,425,120 | 1/1984 | Sampson et al. . |
| 4,459,997 | 7/1984 | Sarstedt . |
| 4,507,117 | 3/1985 | Vining et al. . |
| 4,542,749 | 9/1985 | Caselgrandi et al. . |
| 4,562,844 | 1/1986 | Carpenter et al. . |
| 4,573,976 | 3/1986 | Sampson et al. . |
| 4,592,744 | 6/1986 | Jagger et al. . |
| 4,629,455 * | 12/1986 | Kanno ................................. 604/241 |
| 4,631,057 | 12/1986 | Mitchell . |
| 4,650,468 | 3/1987 | Jennings, Jr. . |
| 4,655,751 | 4/1987 | Harbaugh . |
| 4,675,005 | 6/1987 | DeLuccia . |

(List continued on next page.)

FOREIGN PATENT DOCUMENTS

| | | |
|---|---|---|
| 157409 | 5/1991 | (CN) . |
| 191355 | 9/1992 | (CN) . |
| 225161 | 6/1994 | (CN) . |
| 0278493 | 8/1988 | (EP) . |
| 0327061 | 8/1989 | (EP) . |
| 0347742 | 12/1989 | (EP) . |
| 0 634 183 | 1/1995 | (EP) . |
| 1150980 | 5/1969 | (GB) . |
| WO89/08468 | 9/1989 | (WO) . |
| WO89/12475 | 12/1989 | (WO) . |
| WO90/11099 | 10/1990 | (WO) . |

*Primary Examiner*—Sharon Kennedy
*Assistant Examiner*—Kevin C. Sirmons
(74) *Attorney, Agent, or Firm*—Nixon & Vanderhye (57) ABSTRACT

The syringe includes a barrel, a plunger and an adapter for mounting the needle in the distal end of the barrel. The proximal end of the plunger includes a plurality of circumferentially spaced teeth having radially projecting fingers with contact surfaces. The adapter includes a plurality of circumferentially spaced teeth having undercut surfaces. By advancing the plunger to engage the adapter and rotating the plunger relative to the adapter and syringe barrel, the plunger and adapter are locked to one another. By further rotating the plunger and adapter, the adapter is unscrewed from the barrel end and withdrawn with the syringe needle into the interior of the barrel. The plunger may be broken off adjacent the adapter and inserted, broken end first, into the distal end of the barrel to seal the barrel.

7 Claims, 7 Drawing Sheets

U.S. PATENT DOCUMENTS

| | | |
|---|---|---|
| 4,692,156 | 9/1987 | Haller . |
| 4,695,274 | 9/1987 | Fox . |
| 4,710,170 | 12/1987 | Haber et al. . |
| 4,747,830 | 5/1988 | Gloyer et al. . |
| 4,770,655 | 9/1988 | Haber et al. . |
| 4,774,964 | 10/1988 | Bonaldo . |
| 4,790,822 | 12/1988 | Haining . |
| 4,790,828 | 12/1988 | Dombrowski et al. . |
| 4,795,443 | 1/1989 | Permenter et al. . |
| 4,804,370 | 2/1989 | Haber et al. . |
| 4,810,248 | 3/1989 | Masters et al. . |
| 4,813,426 | 3/1989 | Haber et al. . |
| 4,813,936 | 3/1989 | Schroeder . |
| 4,832,695 | 5/1989 | Rosenberg et al. . |
| 4,838,870 | 6/1989 | Haber et al. . |
| 4,861,338 | 8/1989 | Mathiesen et al. . |
| 4,874,383 | 10/1989 | McNaughton . |
| 4,883,471 | 11/1989 | Braginetz et al. . |
| 4,908,022 | 3/1990 | Haber . |
| 4,919,652 | 4/1990 | Alter et al. . |
| 4,929,232 | 5/1990 | Sweeney et al. . |
| 4,935,015 | 6/1990 | Hall . |
| 4,946,441 | 8/1990 | Laderoute . |
| 4,950,241 | 8/1990 | Ranford . |
| 4,950,251 | 8/1990 | Haining . |
| 4,955,870 | 9/1990 | Ridderheim et al. . |
| 4,978,340 | 12/1990 | Terrill et al. . |
| 4,986,813 | 1/1991 | Blake, III et al. . |
| 4,995,874 | 2/1991 | Strickland . |
| 4,997,423 | 3/1991 | Okuda et al. . |
| 5,007,903 | 4/1991 | Ellard . |
| 5,030,208 | 7/1991 | Novacek et al. . |
| 5,047,016 | 9/1991 | Dolgin et al. . |
| 5,098,402 | 3/1992 | Davis . |
| 5,112,315 | 5/1992 | Gloyer et al. . |
| 5,112,318 | 5/1992 | Novacek et al. . |
| 5,122,124 | 6/1992 | Novacek et al. . |
| 5,152,750 | 10/1992 | Haining . |
| 5,188,597 | 2/1993 | Sweeney et al. . |
| 5,188,601 | 2/1993 | King . |
| 5,205,823 | 4/1993 | Zdeb . |
| 5,205,824 | 4/1993 | Mazur . |
| 5,205,827 | 4/1993 | Novacek et al. . |
| 5,205,833 * | 4/1993 | Harsh et al. ............ 604/240 |
| 5,242,400 | 9/1993 | Blake, III et al. . |
| 5,256,151 | 10/1993 | Chul . |
| 5,263,933 | 11/1993 | Novacek et al. . |
| 5,273,543 | 12/1993 | Bell et al. . |
| 5,304,154 | 4/1994 | Gloyer et al. . |
| 5,308,329 | 5/1994 | Mazur et al. . |
| 5,328,475 | 7/1994 | Chen . |
| 5,336,186 | 8/1994 | Haber . |
| 5,360,404 | 11/1994 | Novacek et al. . |
| 5,401,246 | 3/1995 | Mazur et al. . |
| 5,405,327 | 4/1995 | Chen . |
| 5,414,638 * | 5/1995 | Novacek et al. ............ 604/110 |
| 5,415,638 | 5/1995 | Novacek et al. . |
| 5,462,531 | 10/1995 | Novacek et al. . |
| 5,489,272 | 2/1996 | Wirtz . |
| 5,520,649 | 5/1996 | Novacek et al. . |
| 5,533,970 | 7/1996 | Berger et al. . |
| 5,645,535 | 7/1997 | Goldberg . |
| 5,688,240 * | 11/1997 | Novacek et al. ............ 604/110 |
| 5,746,733 * | 5/1998 | Capaccio et al. ............ 604/411 |
| 5,858,000 * | 1/1999 | Novacek et al. ............ 604/110 |
| 5,871,500 * | 2/1999 | Jepson et al. . |
| 5,882,342 | 3/1999 | Cooper et al. . |
| 5,984,373 * | 11/1999 | Fitoussi et al. ............ 285/92 |

\* cited by examiner

SAFETY SYRINGE WITH RETRACTABLE NEEDLE AND UNIVERSAL LUER COUPLING

TECHNICAL FIELD

The present invention relates to a syringe for medical and industrial applications and particularly relates to a syringe of a type having a needle which can be readily and easily withdrawn into the barrel for disposal purposes, can be sealed at both ends in a manner to reduce the volume of trash upon disposal, provides a double encapsulation of the needle within the syringe for disposal purposes and affords enhanced sealing at the distal end of the barrel as well as other features. Further aspects of the invention include a universal Luer coupling for forming either a Luer fit or a Luer lock.

BACKGROUND

Needlestick injuries among medical practitioners is and has been of tremendous concern because of the possibility for transmission of diseases, for example, the AIDS and Hepatitis B and C viruses and numerous other blood-borne pathogens. The vast majority of currently commercially available syringes do not protect the medical practitioner or those individuals involved in the disposal of syringes from needlestick injuries and consequent possibility of contracting these diseases.

A number of patents disclose syringes having needle-protecting features but most, for various reasons, have not appeared to any significant extent in the marketplace. See, for example, U.S. Pat. Nos. 4,592,744; 4,804,370; 4,542,749; 4,631,057; 4,425,120; 4,258,713; 4,266,544; 4,139,009; 4,774,964 and 4,507,117. These patents have addressed the problem in various ways but none have completely solved the problem or have been a commercial success.

The present invention is a result of various refinements made to assignee's efforts to design, develop and market a safety syringe of the type in which the needle is retractable within the syringe barrel and sealed. Prior syringe designs of applicants' assignee are reflected in U.S. Pat. No. 5,688,240, issued Nov. 18, 1997 and antecedent patents of assignee. While assignee's design demonstrates superior capabilities vis-a-vis the designs of the above-listed prior patents, further refinements as set forth herein are believed necessary to provide a fail-safe, easily usable retractable needle syringe. For example, in the prior design illustrated in assignee's U.S. Pat. No. 5,688,240, the disclosure of which is incorporated herein by reference, the connection between the plunger and needle-carrying adapter could be disrupted by forceful withdrawal of the plunger subsequent to that connection and prior to complete unthreading of the adapter relative to the barrel. While this might occur only rarely, if at all, there remained the possibility that the adapter could be left in the barrel end in a loosened condition leaving exposed a contaminated needle and potentially permitting leakage of fluids from the syringe. Additionally, while assignee's prior patent demonstrated a capacity to seal both ends of the syringe barrel for disposal, it relied on a threaded connection between the proximal end of the plunger, after it was broken off from the adapter, for threaded sealing engagement with the distal end of the barrel. While both ends of the barrel were fluid-sealed, this resulted in an elongated structure which, from a disposal standpoint, disadvantageously increased trash volume. Other refinements and improvements to assignee's prior syringe will be evident from the ensuing description.

DISCLOSURE OF THE INVENTION

In accordance with the present invention, there is provided a syringe comprised of an elongated, generally cylindrical barrel, having a reduced diameter distal end with female threads and a proximal end having at least one radially inwardly extending circumferential rib. The distal end of the barrel threadedly receives an adapter for mounting a needle, either as a Luer fit or Luer Lok or a needle integrally formed with the adapter whereby the passage through the needle and through the adapter affords communication between the interior of the barrel and the tip of the needle. A plunger is receivable in the barrel through its proximal end and has a distal end portion carrying a bung for sealing against the interior walls of the barrel. The proximal end of the plunger has a finger press which, in combination with a flange at the proximal end of the barrel, enables the practitioner to manipulate the plunger axially within the barrel.

In one aspect of the present invention, there is provided a unique engagement structure on the proximal and distal ends of the adapter and plunger, respectively, generally enabling the plunger to be pushed axially home to engage the adapter and unscrew the adapter from the barrel end, permitting the adapter with the needle carried thereby to be withdrawn into the interior of the barrel. As described in detail below, the adapter is withdrawn to the proximal end of the barrel. The projecting plunger body can then be snapped from the distal end of the plunger leaving the bung sealing the proximal end of the barrel and then inserted, broken end first, into the opposite distal end of the barrel. The plunger body is open in an axial direction along its centerline and, when fully inserted into the barrel, substantially surrounds but does not functionally contact the needle withdrawn in the barrel. The plunger also seals the distal end of the barrel upon full insertion whereby any fluids within the barrel and in prior contact with the needle are sealed in the barrel. It will be appreciated that this arrangement reduces the volume of the sealed syringe upon disposal in comparison with the volume of the syringe of the type illustrated in assignee's prior U.S. Pat. No. 5,688,240.

The unique engagement structure between the plunger and adapter of the present syringe includes an adapter engagement structure on the distal end of the plunger comprising a plurality of circumferentially spaced, teeth about a central recess, e.g., a bulbous recess, extending axially toward the adapter. Surrounding a central axially projecting bulbous portion of the adapter are a plurality of circumferentially spaced teeth projecting axially toward the plunger and forming mating engagement structure on the adapter. The plunger teeth as viewed from the side of the plunger looking toward the axis are generally triangularly-shaped, each terminating in an apex with at least one sloped or inclined side surface and an axially extending circumferentially facing drive surface along respective opposite sides of the apex. The plunger teeth also include a finger adjacent the apex end of each tooth which projects in a radial outward direction, leaving a recess between an axially facing contact surface of the finger and a base portion of the distal end of the plunger.

The mating engagement structure on the adapter includes a plurality of circumferentially spaced, axially extending teeth which, as viewed looking from the side toward the axis, have generally right triangularly-shaped projections terminating in apices. Each tooth has one inclined or sloping surface on one side of the apex and a driven surface on the opposite side of the apex. The teeth include a generally triangularly-shaped lug which is spaced radially outwardly of the hub of the adapter and has an axially facing contact surface, i.e., an undercut, spaced from an annular seat forming part of the adapter. When the plunger is pressed axially to engage the adapter, it will be appreciated that each plunger tooth will engage one of the sloping surfaces of the adapter teeth, i.e., either the sloping surface of the tooth or of the lug. Upon further axial movement of the plunger into the barrel relative rotation of the plunger and adapter will occur to locate the apices of the plunger teeth at the lands between the adapter teeth. When the plunger has been pressed into its furthest axial position, the axially facing surfaces of the plunger and adapter teeth are enabled for engagement with one another upon relative rotation of the plunger and adapter. That is, when the plunger and adapter teeth are relatively rotated to engage the plunger drive surfaces against the adapter driven surfaces, the contact surfaces of the fingers on the plunger underlie the oppositely axially facing contact surfaces, i.e., undercuts, of the lugs of the adapter. Upon further rotation of the plunger relative to the adapter and barrel, the adapter is unthreaded from the distal end of the barrel, freeing it from the barrel. Consequently, the adapter and needle carried by the adapter can be withdrawn into the interior of the barrel upon withdrawal of the plunger toward the proximal end of the barrel.

A unique aspect of the present invention resides in a cooperation between the adapter and mating engagement structures on the plunger and adapter, respectively, to afford substantial initial resistance to relative rotation of the plunger and adapter after the plunger has been pressed into full engagement with the adapter. This enables the plunger to be freely withdrawn after initial engagement of the structures with one another prior to locking the plunger and adapter to one another. To provide this initial resistance, a protuberance, for example, a radially projecting rib and preferably a plurality of ribs are provided on one of the adapter and mating engagement structures, preferably on the mating engagement structure on the adapter and between the teeth. When the plunger teeth are oriented to locate the apices of the teeth in the lands between the teeth of the adapter upon full axial engagement of the plunger with the adapter, the forward (driving) faces of the plunger teeth lie on one side of the ribs, affording initial and substantial resistance to rotation of the plunger relative to the adapter. The practitioner may sense this initial resistance and recognize that the plunger may still be axially withdrawn relative to the adapter. When the practitioner consciously rotates the plunger relative to the adapter to overcome the resistance, however, the ribs cause the plunger teeth to flex slightly radially outwardly as the fingers of the plunger teeth engage below the lugs of the adapter teeth and the plunger is rotated toward a locked position with the adapter.

In a further aspect of the present invention, the adapter and mating engagement structures of the plunger and adapter, respectively, are locked to one another prior to unscrewing the adapter from the barrel and after the plunger and adapter are relatively rotated to engage the driving and driven surfaces with one another. To accomplish this, the inside faces of the plunger teeth have recesses for receiving the ribs of the adapter. Consequently, when the plunger is rotated to fully engage the contact surfaces of the engagement structures with one another, i.e., the fingers and undercuts, and to engage the driving and driven surfaces, the recesses register with the ribs to enable the plunger teeth to resiliently flex radially inwardly to receive the ribs, hence locking the plunger and adapter to one another. The practitioner, when rotating the plunger relative to the barrel to lock the plunger to the adapter may sense this detenting action of the rib and recess and recognize that (i) the plunger and adapter have been locked to one another and (ii) further rotation of the plunger in the same direction relative to the barrel will cause the adapter to unthread from the distal end of the barrel. Consequently, it is practically not possible to pull back the plunger after the plunger has been rotated relative to the barrel to only partially unscrew the adapter because of the engagement of the fingers and undercuts and the ribs and recesses.

In a further aspect of the present invention which affords significant reduction of the volume of trash once the syringe has been used and requires disposal, the plunger includes a body preferably having a cross-section with an open center. For example, and preferably, a generally channel-shaped plunger body cross-section is provided between the finger press and the distal end of the plunger. Areas of weakness are provided between the plunger body and the distal end of the plunger to enable the plunger body to be broken upon full withdrawal of the adapter into sealing engagement with the proximal end of the barrel. By snapping the plunger body from the distal end of the plunger and inserting the plunger body broken end first through the distal end of the barrel, the channel-shaped body portion is received about the withdrawn needle within the interior of the barrel. When fully inserted, the needle within the barrel is surrounded by essentially two layers of plastic material and lies out of contact with the plunger body.

Preferably, the plunger body adjacent its proximal end has a pair of circumferentially extending feathered ribs spaced one from the other. The distal end of the barrel has a radially inwardly directed shoulder. When the plunger body is inserted into the distal end of the barrel, the first rib passes over the shoulder and the second rib facing in the opposite direction abuts the threads on the other side of the shoulder to form a seal. A third feathered rib may be provided on the plunger body for cooperation with a tapered or feathered end of the barrel to provide a secondary seal. Consequently, with the adapter sealed at the proximal end of the barrel and the plunger body sealing the distal end of the barrel, the fluids within the barrel and those in contact with the needle are completely sealed within the barrel.

A still further aspect of the present invention provides for enhanced sealing between the adapter and the distal end of the barrel. The adapter is formed of plastic material which is harder than the plastic material of the barrel. Consequently, when the adapter is screwthreaded into the barrel, an effective seal is formed. To further enhance and provide further assurances that the barrel end of the syringe is sealed by the adapter, a further annular seal may be provided adjacent the base of the threads on the adapter, for example, on the adapter disk. The seal preferably has a V-shaped sealing surface to accommodate positive and negative pressures within the barrel, i.e., one or the other of the legs of the seal bears more tightly against the barrel in response to positive and negative pressures, respectively. The feathered seal may be readily formed in a double-molding process.

In a further aspect, there is provided a plastic material shrink-wrapped about the syringe for maintaining the syringe sterile. An added tear-off tab of plastic material at the distal end of the barrel enables the Luer needle to be secured to the cone of the adapter without removing the remaining plastic material about the syringe barrel. A second added tear-off tab of plastic material at the proximal end of the barrel enables the plastic material to part, permitting movement of the plunger relative to the barrel. This maintains the sterility of the syringe until just prior to use and facilitates use without extensive removal of the shrink-wrapped plastic material about the syringe barrel.

In a still further aspect of the present invention, the adapter is provided with a pair of diametrically opposite mounting elements spaced from the axially projecting cone which mounts the needle to the adapter. The elements first project axially from the adapter body and then form two flanges which extend circumferentially about the cone, leaving spaces between the two flanges. The two flanges permit the standard Luer needle to be retained on the adapter as a Luer fit or a Luer lock. It will be appreciated that the standard Luer needle has a generally conically-shaped hollow needle hub terminating at one end in the projecting needle and at its opposite end in a pair of diametrically radially outwardly directed flanges. The Luer needle may be attached to the adapter as a Luer fit by engaging the hub of the needle over the cone of the adapter, the flanges of the needle hub being received between the flanges of the adapter. Alternatively, the Luer needle may be locked to the adapter to form the Luer lock by engaging the hub of the needle on the adapter cone to locate the hub flanges axially beyond the adapter flanges and then rotating the Luer needle relative to the adapter. The rotation causes the flanges of the Luer needle hub to bear against the inclined surfaces of the flanges, i.e., threadedly engage the flanges, thereby providing the standard threaded Luer lock.

It will also be appreciated that the adapter flanges are inside the outer diameter of the needle hub flanges. This is significant in that it enables a very slim design as the minimum barrel inside diameter is determined by the outer diameter of the flanges on the needle hub, plus, two material thicknesses of the cylindrical wall of the barrel and adapter. With the present design, the flanges of the adapter are flush with the outside diameter of the needle hub flanges and thus the minimum diameter is significantly reduced. This is also significant in the manufacture of the syringe. When threads are put on the inside of a cylinder, e.g., in a syringe barrel or adapter to accommodate a Luer needle in a Luer lock, the core of the mold is necessarily unscrewed during manufacturing to avoid disruption of the threads. By providing flanges on the adapter, a rotating core is not required. Further, the adapter flanges reduce the quantity of plastic material to that required for two small flanges rather than a complete cylinder, a significant savings in material. Finally, the inclusion of the flanges enables substantial increases in the productivity of the mold, i.e., the number of adapter units produced per unit time. This is because the speed of cooling of the material of the mold is a function of the quantity of the material being molded. Therefore, if the quantity of material is reduced, the material in the mold cools more rapidly, with the result that the mold cycle time can be increased.

The standard Luer needle may also be modified in accordance with this invention to provide a threaded assist, in the case of a Luer lock, when removing the Luer needle from the adapter cone. The Luer needle hub may be provided with an additional pair of flanges spaced axially from the end flanges to engage the sloped undersurfaces of the adapter flanges. When the Luer needle is rotated relative to the adapter in a direction to unlock and remove the Luer needle, the additional flanges of the Luer needle and the undersurfaces of the adapter flanges cooperate to unthread the Luer needle from the adapter, breaking the functional connection between the Luer hub and the adapter cone.

It will be appreciated that the foregoing described Luer coupling between the needle and the adapter used in the syringe hereof has much broader application and could be used to connect any number of different items. For example, the Luer coupling hereof may be used to connect a flexible intravenous line and a transducer or two flexible intravenous lines as an extension. It can be used to couple a syringe and an intravenous line and, in general, can be used in any application in which current standard Luer connections are made.

In a preferred embodiment according to the present invention, there is provided a syringe comprising a hollow axially elongated barrel having distal and proximal ends, an adapter secured to the barrel adjacent the distal end thereof for carrying a needle, the adapter being releasable from the barrel in response to relative rotation between the barrel and the adapter, a plunger axially movable in the hollow interior of the barrel, an adapter engagement structure disposed at a distal end of the plunger and engageable with a mating engagement structure on the adapter in response to axial movement of the plunger toward the distal end of the barrel, the structure being cooperable to (1) lock the plunger and the adapter to one another in response to relative rotation of the plunger and adapter and (2) cause the adapter and the needle carried thereby to part from the end of the barrel in response to subsequent rotation of the plunger and the adapter locked thereto relative to the barrel, thereby enabling the adapter and the needle carried thereby to be withdrawn into the interior of the barrel when the plunger is withdrawn away from the distal end of the barrel.

In a further preferred embodiment according to the present invention, there is provided a syringe for mounting a needle having a cylindrical hub open at one end, a pair of flanges spaced from one another about the hub, and a needle projecting from the hub at an opposite end, comprising a plunger axially movable in the hollow interior of the barrel, a needle mounting structure adjacent the distal end of the barrel for mounting the needle on the syringe and including a needle mounting hub and a pair of flanges spaced radially from the needle mounting hub and from one another, the flanges having surfaces facing the proximal end of the barrel enabling reception of the needle hub about the needle mounting hub and engagement of the needle hub flanges and the flange surfaces upon rotation of the needle hub relative to the needle mounting hub.

In a still further preferred embodiment according to the present invention, there is provided a universal Luer coupling comprising a body having a generally frustoconical male part having an axis and a first diameter and a second diameter smaller than the first diameter, the body terminating in an end adjacent the second diameter, the body having a pair of locking elements spaced from the cone and having inclined surfaces facing generally away from the second diameter, a female hub having an axis and a recess opening through one end of the hub for receiving the male part, the hub including a pair of flanges about the hub opening at generally diametrically opposed sides of the hub, the hub being receivable about the male part with the smaller diameter thereof disposed within the hub and the axes of the male part and the hub lying generally coincident with one another, the hug flanges engaging along the inclined surfaces when the hub is received about the male part to tightly engage the hub and the male part to one another in response to relative rotation of the hub and the male part in a direction causing the hub to advance toward the large diameter of the male part.

Accordingly, it is a primary object of the present invention to provide a novel and improved retractable needle syringe having various advantages in manufacture, construction, operation and use as compared with prior syringes of this general type and among which advantages include the following:

(1) An improved engagement structure between the plunger and adapter, enabling the plunger to be withdrawn without locking to the adapter after the plunger has been pressed fully home against the adapter.

(2) A plunger and adapter engagement structure which affords initial resistance to rotation of the plunger relative to the adapter toward the locking position, enabling the practitioner to recognize by feel when the plunger has been moved relative to the adapter toward the locking position.

(3) A detenting action in the engagement structure enables the practitioner to recognize that the plunger has been locked to the adapter.

(4) Withdrawal of the plunger from the adapter upon only partial unscrewing of the adapter from the barrel is prevented.

(5) The volume of the syringe upon disposal is substantially reduced.

(6) The withdrawn needle lies along the axial centerline of the barrel and is encapsulated without contact by essentially two layers of plastic material formed by the barrel and plunger body.

(7) Seals are provided at the opposite ends of the barrel for disposal of the used syringe whereby leakage of fluids from the barrel is prevented.

(8) Needle mounting flanges on the adapter enable the standard Luer needle to be secured to the adapter in a Luer fit or Luer lock.

(9) The Luer needle is modified to assist, in cooperation with flanges on the adapter, removal of the needle from the adapter.

(10) Enhanced sealing is provided between the adapter and barrel at its distal end.

(11) A sterile syringe utilizing plastic material, preferably shrink-wrap plastic material, to maintain sterility is provided while affording ready and easy application of the needle to the syringe and use of the syringe without removal of most of the plastic wrapping material, i.e., a substantial reduction of packing trash.

(12) A double-molded additional plastic seal at the distal end of the barrel to enhance sealing.

The Luer coupling hereof in general application has the capability of being manufactured with less material than the standard Luer coupling having a cone with an overlying internally threaded cylindrical extension, assists in disconnecting the Luer coupling is less expensive than the standard Luer coupling and can be employed in any connection in which a standard Luer connection is employed.

BEST MODE FOR CARRYING OUT THE INVENTION

Figure 1:
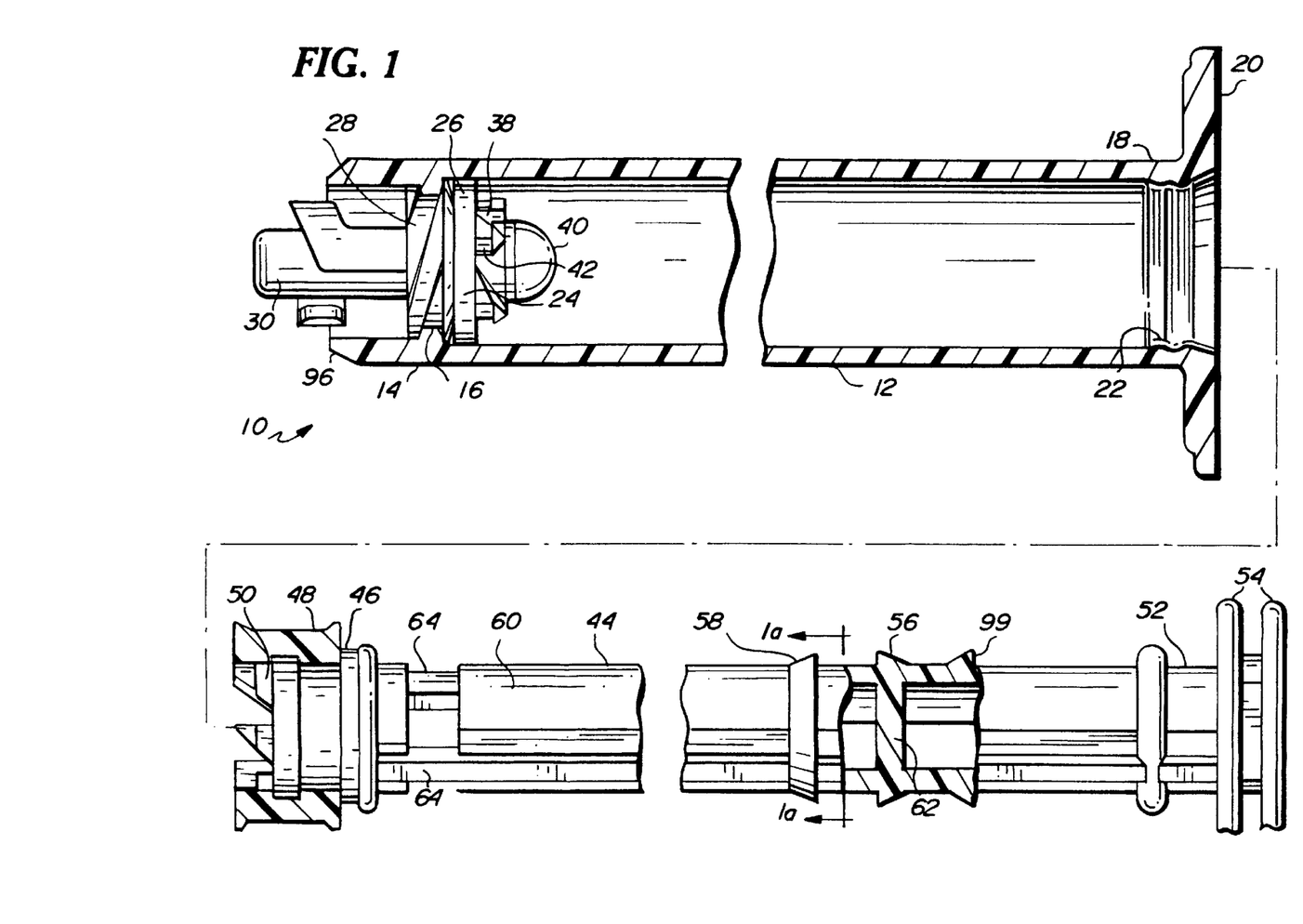
FIG. 1 is a fragmentary cross-sectional view of a syringe according to the present invention having a syringe barrel and plunger shown apart from one another for clarity of illustration.
Figure 1A:
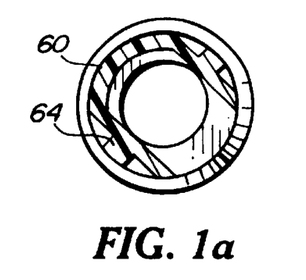
FIG. 1a is a cross-sectional view thereof taken generally about on line 1a—1a in FIG. 1.
Figure 6:
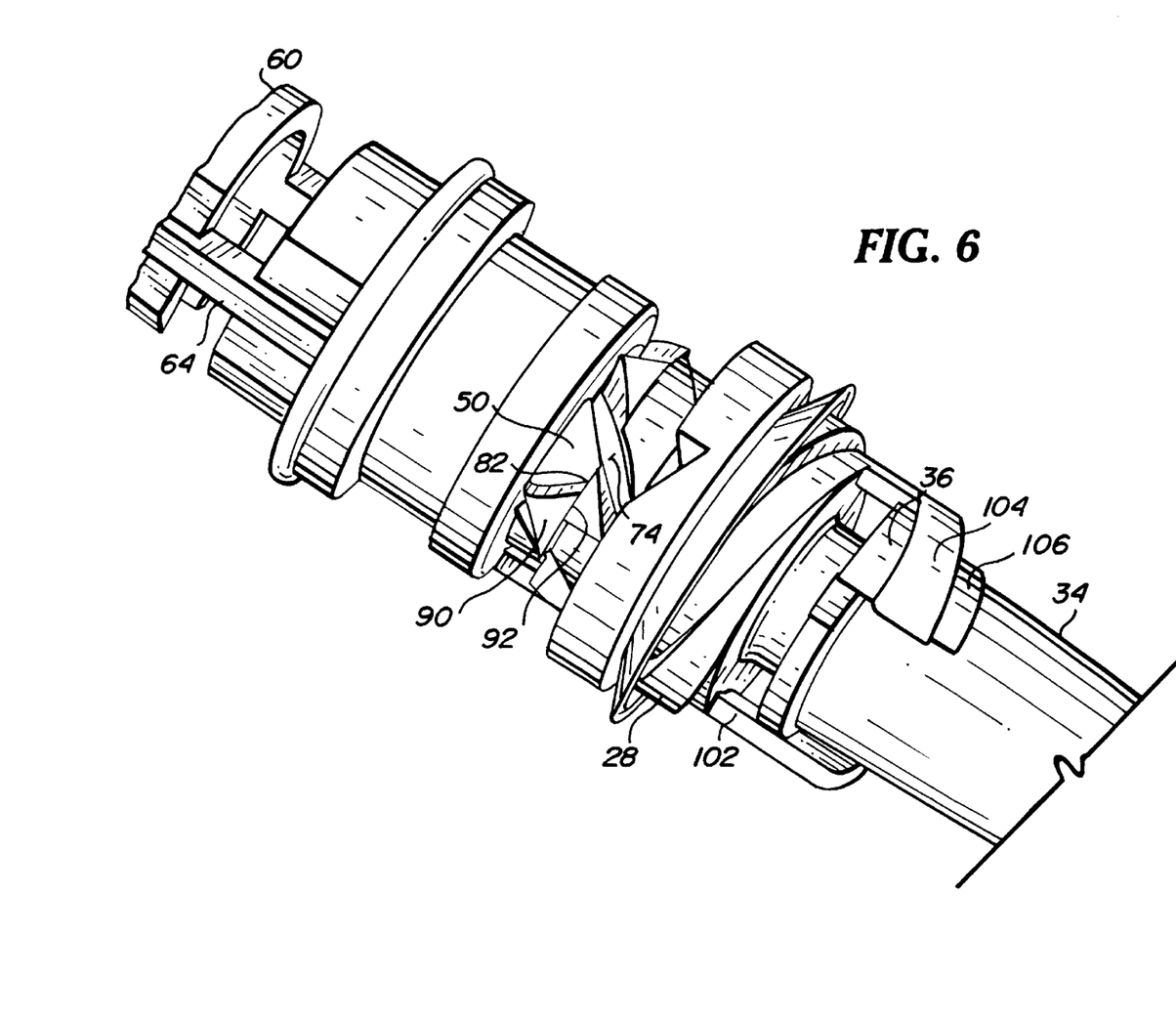
FIG. 6 is a view similar to FIG. 4 with the plunger and adapter relatively rotated into a locked position.
Figure 7:
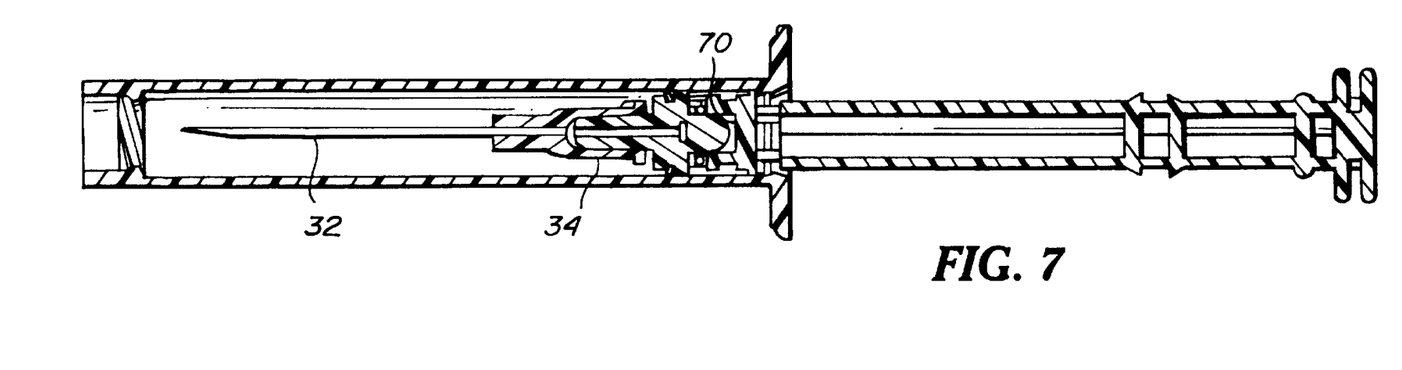
FIG. 7 is a cross-sectional view illustrating the position of the plunger and adapter relative to the barrel after withdrawal of the adapter and needle into the syringe barrel.
Figure 8:
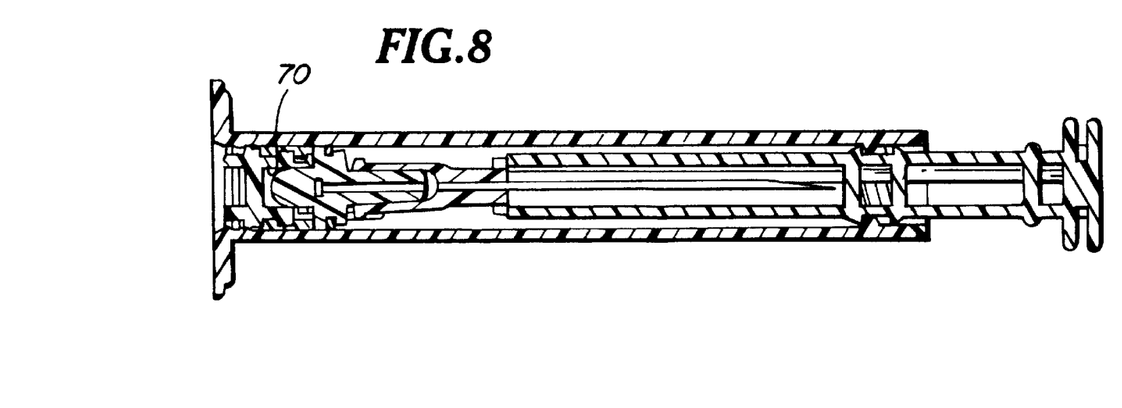
FIG. 8 is a view similar to FIG. 7 illustrating the insertion of the plunger, broken end first, into the distal end of the barrel to seal the distal end.

Referring now to the drawings, particularly to FIG. 1, there is illustrated a syringe, generally designated 10, constructed in accordance with the present invention. Syringe 10 includes an elongated, generally cylindrical barrel 12 having a reduced diameter distal end 14 with internal threads 16 forming a shoulder. The barrel may be formed of a plastic material, such as polypropylene. The proximal end 18 of the barrel is open and includes a finger press 20 projecting radially outwardly in the form of a pair of diametrically opposite flanges, as well as a pair of radially inwardly extending, circumferential ribs 22. As illustrated in FIG. 1, the distal end 14 of barrel 12 threadedly receives an adapter 24. Adapter 24 generally comprises a central cylindrical section, i.e., an annular disk 26 having a reduced diameter cylindrical hub including male threads 28 for threading the adapter to the threads 16 on the distal end 14 of barrel 12. The adapter may be formed of a plastic material, such as polystyrene or a polycarbonate. If desired, the adapter may also be formed of metal. Adapter 24 also includes a surface of revolution, e.g., a reduced diameter cone or male part 30 projecting axially of threads 28 for mounting a hollow needle 32 (FIG. 7). The needle 32 may be integrally formed with the adapter and permanently attached thereto. Alternatively and preferably, the needle comprises a standard Luer needle which, as illustrated in FIGS. 6–8 and with the exception of flanges 106, includes a hub 34 having a hollow open end defined by a frustoconical surface and an opposite end terminating in the projecting needle 32. The hub 34 includes a pair of radially outwardly diametrically opposed flanges 36 (FIG. 6). The hub 34 and needle 32 in assembly with the male part 30 define an axis A through the needle 32 and the central opening 44 through the adapter. As set forth in detail hereafter, the standard Luer needle may be applied to the adapter as a Luer fit or as a Luer lock. The opposite end of the adapter terminates in a central, preferably bulbous portion 40 projecting axially from hub 38, the cylindrical hub 38 carrying a plurality of teeth 42, described in detail below.

Syringe 10 also includes a plunger 44 including a distal end 46 about which is received a bung 48 (FIG. 1) for sealingly engaging the interior walls of the barrel (FIGS. 3–6 illustrate the distal end of the plunger without the bung for clarity). It will be appreciated that the bung can be replaced by a plastic part carried by the plunger causing an interference fit with the barrel. Plunger end 46 terminates in a plurality of projections, e.g., teeth 50, described in detail below. The proximal end 52 of plunger 44 is generally cylindrical in cross-section, terminating in a pair of axially spaced flanges 54 forming a thumb press. Axially inwardly of the thumb press are a pair of oppositely feathered, radially outwardly projecting surfaces 56 and 58 for sealing the distal end 14 of barrel 12 upon disposal of the syringe, also as described below. The plunger body 60 between the sealing surface 56 and the distal end 46 is preferably channel-shaped, although as will be clear from the ensuing description, the plunger body may have a different cross-sectional shape such as circular or square. Importantly, the centerline of the plunger body 60 remains open from a location adjacent the distal end 46 to a closed end 62 of the plunger body where the channel-shape transitions to a circular shape and which circular shape continues to the proximal end of the plunger. The plunger 44 includes a pair of weakened portions 64 connecting the plunger body 60 and the distal end 46. While the weakened portions 64 are illustrated as a pair of tenons along opposite sides of the plunger connecting the distal end 46 with the channel-shaped plunger body 60, other types of weakening may be used such as a perforated connection.

Before discussing the constructional details of the syringe, a very general description of the usage of the syringe will now be provided to facilitate further understanding of the invention. When the medical practitioner receives the syringe, the sterile packaging described later is disrupted and the Luer needle is applied to the cone 30 of the adapter 24 in either a Luer fit or Luer lock, as described below. Once the Luer needle is attached, the medical practitioner proceeds in conventional manner to withdraw fluids into the barrel of the syringe, change the needle as needed and express the fluids from the barrel through the needle in known fashion. Once used, the syringe must be safely disposed. To accomplish this, the plunger 44 is pressed inwardly to engage the distal end 46 with the adapter 24 and particularly to engage the engagement structures, i.e., the teeth on the plunger with the teeth on the adapter. Upon rotation of the plunger relative to the barrel and adapter, the plunger and adapter teeth engage and lock to one another whereby the plunger and adapter are locked together. Upon further rotation of the plunger relative to the barrel, the adapter is unscrewed from the distal end of the barrel. With the adapter locked to the plunger, the plunger and adapter, together with the needle carried by the adapter, may be withdrawn into the barrel. Upon withdrawing the adapter to the proximal end of the plunger, the plunger is broken off at weakened portions 64 and the plunger body 60 is inserted, broken end first, into the now open distal end of the barrel. By pressing the plunger into the barrel, the first seal 58 on plunger body 60 passes over the threads 16 of the barrel, while the second seal 56 engages the threads to seal the plunger in the distal end of the barrel. It will be appreciated that by inserting the plunger body, broken end first, into the barrel, the channel-shaped section of the plunger body surrounds or encapsulates but does not functionally contact the needle projecting from the adapter into the barrel at its proximal end. Consequently, essentially two layers of plastic material surrounding the needle and its tip. Having described the general usage of the syringe and the manner of its disposal, various constructional aspects of the syringe will now be described in detail.

Referring back to FIG. 3, the adapter engagement structure formed on the distal end 46 of plunger 44 includes a plurality of teeth 50 which project axially from distal end 46 and are spaced circumferentially from one another. A recess 70 (FIGS. 7 and 8) is formed centrally within the distal end 46 of the plunger 44, complementary in shape to the central portion 40 of the adapter such that the central portion 40 may be guidedly received in the recess 70 upon engagement of the plunger and adapter. As viewed from the side and looking toward the axis of the plunger, the teeth 50 are substantially triangular in shape, each terminating in an apex 72. A sloping or inclined surface 74 extends to the base of each tooth 50 along one side of the apex 72, while a drive surface 76 extends from the apex 72 toward a base 75 of the distal end 46 of the plunger 44 in a plane generally parallel to the plunger axis. Each tooth 50 also includes a radially outwardly projecting finger 78 (FIGS. 3–4) forming a recess 77 between an axially facing contact surface 82 of finger 76 and the base 75 of the distal end 46. Also, along the inner surface of each tooth is a generally axially extending recess, e.g., a groove 80 spaced slightly behind the drive surface 76 of the tooth 50. This adapter engagement structure engages a mating engagement structure on the adapter 24, which will now be described.

Figure 2:
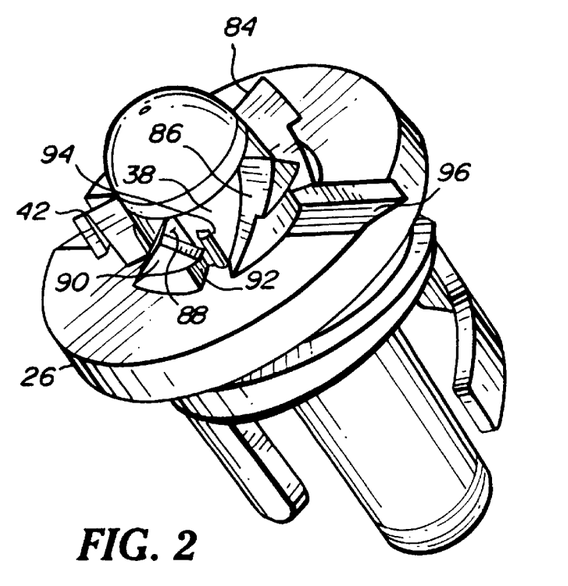
FIG. 2 is a perspective view of an adapter according to the present invention.
Figure 3:
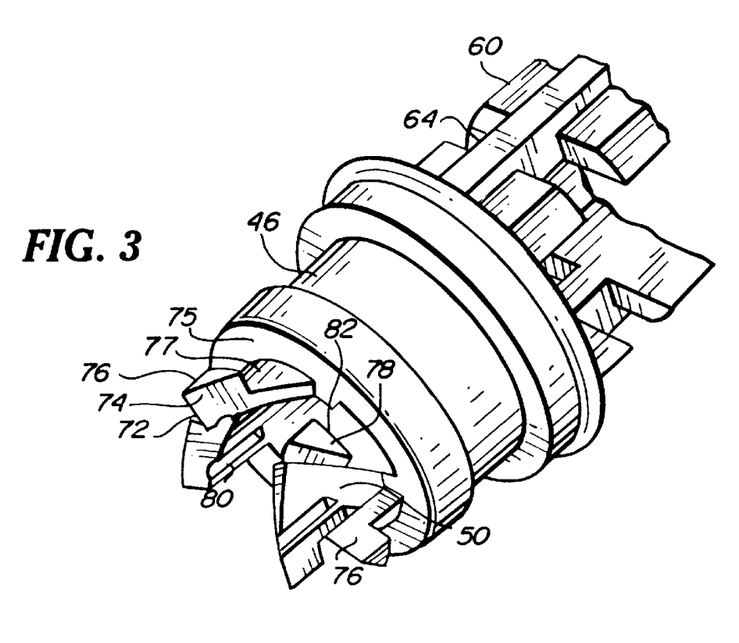
FIG. 3 is an enlarged perspective view of the distal end of the plunger illustrating the adapter engagement structure.
Figure 4:
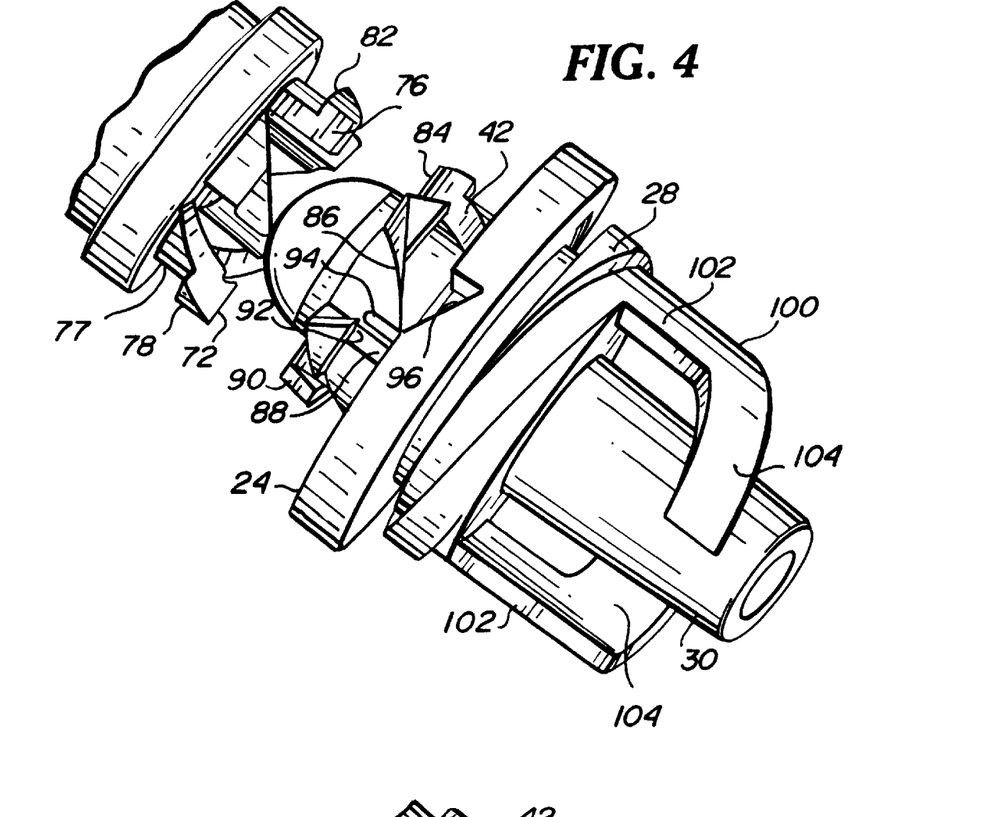
FIG. 4 is a fragmentary perspective view illustrating the distal end of the plunger and the adapter just prior to engagement.
Figure 5:
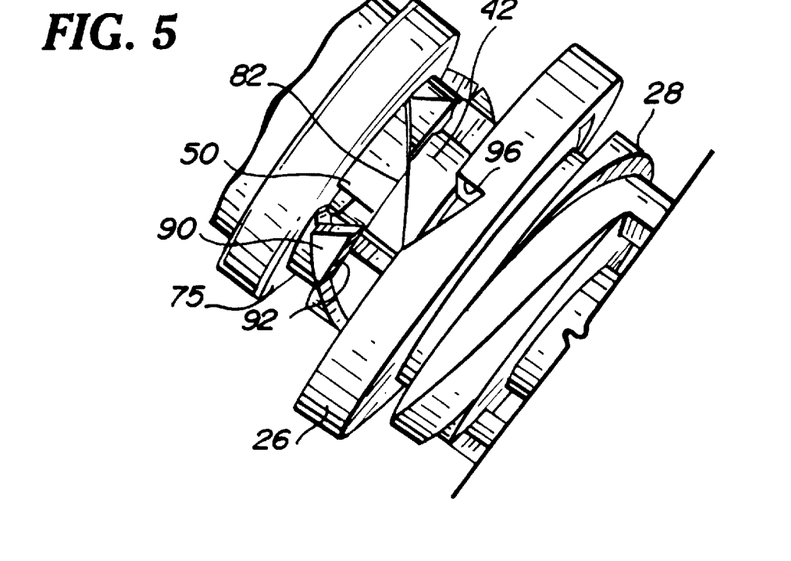
FIG. 5 is a view similar to FIG. 4 with the plunger and adapter engaged prior to rotation into the locked position.

Referring to FIGS. 2 and 4, the teeth 42 of the adapter 24 extend axially from the disk 26 and are circumferentially spaced from one another. As viewed from the side, looking toward the axis of the adapter, the teeth 42 are generally right-triangularly-shaped, each terminating in an apex 84 having a sloping or inclined surface 86 extending from apex 84 to the disk 26. On the opposite side of each tooth 42 is a driven surface 88 which extends in a generally axial direction from the apex to the disk 26. Each tooth 42 also includes a generally triangularly-shaped lug 90 spaced radially outwardly of the cylindrical hub 38 of adapter 24 and which has an axially facing contact surface 92 which projects beyond the driven surface 88 of the tooth 42 in a circumferential direction, forming an undercut spaced from the disk 26. Additionally, the cylindrical hub 38 of the adapter includes a radially extending protuberance, e.g., a radially outwardly projecting axially extending rib 94 between each driven surface 88 of one tooth and the sloped surface 86 of an adjacent tooth.

It will be appreciated that the adapter 24 has a central axial passageway which extends from the needle end of the adapter axially into the cylindrical hub 38. A pair of vent passages or grooves 96 extend radially from the central cylindrical hub 38 and along the disk 26 in communication with the needle and the axial passageway through the adapter. Preferably, grooves 96 have a right triangular shape in cross-section with the vertical face of the groove in the appropriate sense for engagement by a tool to screw home the adapter. By providing grooves 96 in communication with the axial passageway, the grooves and passageway will assume the most superior position within the interior of the barrel when the syringe is oriented vertically with the needle uppermost. When the plunger is advanced toward the needle end to vent air from the interior of the barrel, any air trapped within the barrel between the plunger and adapter will vent through the grooves into the central passage, thus purging all air from the barrel prior to injection. More particularly, the triangularly-shaped cross-sections of the grooves 96 reduce the deadspace in the syringe when the bung is fully compressed against the interior face of disk 26 thereby enabling a more complete emptying of the syringe as the plunger is forcefully pushed home during injection.

The manner in which the plunger and adapter are locked to one another for withdrawing the adapter and the needle carried thereby into the barrel will now be described in detail. After use of the syringe, and for disposal purposes, the practitioner presses the plunger toward the adapter. As the plunger is advanced, the adapter engagement structure on the plunger and the mating engagement structure on the adapter cooperate to relatively rotationally align the plunger and adapter into a position for subsequent locking of the plunger to the adapter and release of the adapter from the distal end of the barrel. To accomplish this, it will be appreciated that as the plunger is axially displaced toward the adapter, the apices 72 of the plunger teeth will engage either the sloping surfaces 86 of the adapter teeth or the sloping surfaces of the lugs 90 on the opposite sides of apices 84 from the sloping surfaces 86. Upon such engagement and further axial displacement of the plunger, the engaged sloping surfaces will rotationally cam the plunger relative to the adapter to axially align the apices 72 of the plunger teeth 50 in the lands or bases of the spaces between adjacent adapter teeth 42. When the plunger has been pressed axially home, the contact surfaces 82 of plunger teeth 50 lie slightly below the contact surfaces 92 of lugs 90. With the distal end of the plunger seated in the adapter, the practitioner may still withdraw the plunger from the adapter for repeated unimpeded full axial movement because the plunger has not yet been locked to the adapter.

A feature of the present invention provides for an initial resistance to rotation of the plunger relative to the adapter which precludes premature inadvertent engagement of the plunger and adapter which would prevent withdrawal of the plunger from the adapter. To accomplish this, the driving surfaces 76 of the plunger teeth bear against the radially projecting ribs 94 on the adapter to offer initial resistance to rotation of the plunger relative to the adapter in one direction. The practitioner senses this initial resistance and recognizes that the plunger may yet be axially withdrawn relative to the adapter. To continue the disposal procedure, however, the practitioner purposefully rotates the plunger relative to the adapter to overcome this resistance, typically in a right-handed and threading rotational direction. Rotation of the plunger relative to the adapter in the opposite direction only causes a ratcheting action between the plunger and adapter, thus alerting the practitioner that the plunger and adapter should be rotated in the opposite threading direction to continue the disposal procedure. As the plunger and adapter are relatively rotated to cause the plunger teeth 50 to ride over the ribs 94, the ribs 94 resiliently flex in a radial outward direction. Simultaneously, the contact surfaces 82 and 92 on the fingers 78 and lugs 90, respectively, register and lie in contact one with the other. Upon completion of the relative rotation of the plunger and the adapter, the driving surfaces 76 of the plunger teeth 50 engage the driven surfaces 88 of the adapter teeth 42.

Simultaneously, the grooves 80 of the plunger teeth 50 register with the ribs 94 of the adapter, enabling the plunger teeth 50 to resiliently flex inwardly to engage the ribs 94 in the grooves 80 thereby locking the adapter engagement structure of the plunger and the mating engagement structure of the adapter to one another. The inward movement of the teeth 50 is caused by the return bias of the resilient teeth 50 after first having been resiliently flexed outwardly to ride over the ribs. The practitioner senses this detenting locking action of the elements 80 and 94 and recognizes that further rotation of the plunger in the same direction will unscrew the adapter from the distal end of the barrel, freeing the adapter for withdrawal with the plunger and the needle carried by the adapter into the interior of the barrel. It will be appreciated that the distal end of the plunger and the adapter remain locked during withdrawal into the barrel interior such that the needle remains in substantial axial alignment with the barrel up to and including sealing the adapter in the proximal end of the barrel, as illustrated in FIG. 7.

To complete the disposal procedure, the practitioner withdraws the plunger to the extent that the bung 48 engages the rib 26 at the distal end of the barrel and seals at that end. When the plunger cannot be withdrawn further, the practitioner breaks the plunger body 60 from the distal end 46 of the plunger 44 at the weakened connection 64 and inserts the plunger body 60, broken end first, into the now open distal end of the barrel. Upon insertion, it will be appreciated that the channel-shaped cross-section of the plunger body 60 substantially surrounds the needle projecting from the adapter. The practitioner advances the plunger body into the barrel such that the first feathered surface 58 resiliently detents past the shoulder, while the second sealing surface 56 butts against the shoulder comprised of threads 16. At this time, the practitioner will recognize, due to this detenting action, that the plunger body has been fully inserted into the barrel and that the needle is substantially completely encapsulated by the plunger body as well as wholly by the barrel itself. Also, both ends of the barrel are now sealed, preventing outflow of residual fluid from the barrel and needle. Particularly, the bung at the distal end of the plunger seals the proximal end of the barrel, while the seals 56 and 58 on the plunger body seal the distal end of the barrel.

To further ensure an effective seal at the distal end of the barrel, the end of the barrel may have a tapered surface 96 and an additional rib 98 having a feathered surface 99 may be formed on plunger body 60 inwardly of the finger press. When the seals 56 and 58 engage the shoulder, the surfaces 96 and 99 engage one another to form an additional seal.

Figure 11:
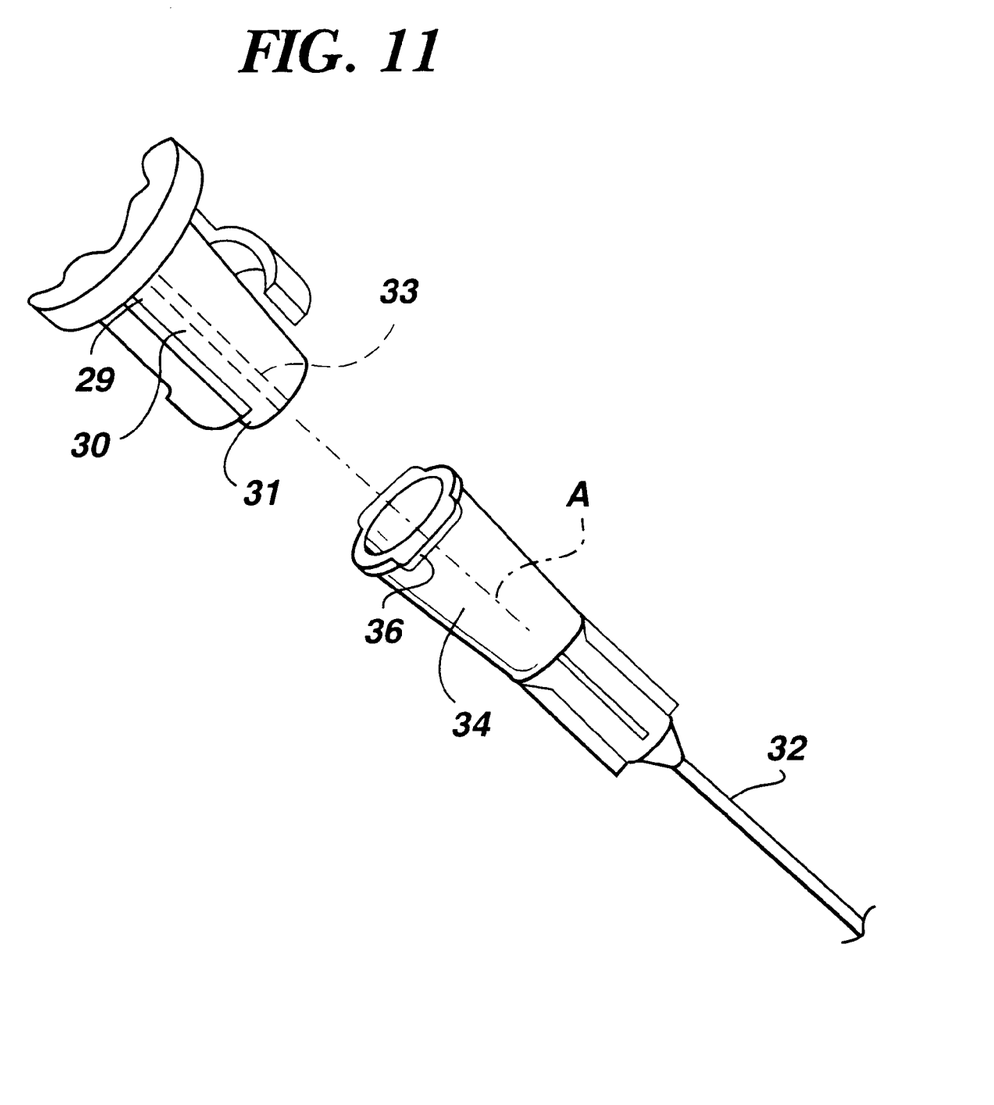
FIG. 11 is a fragmentary exploded perspective view illustrating the Luer needle and the male part of the adapter prior to their coupling.

A significant feature of the present invention resides in the novel and improved connection between the Luer needle and the adapter. It will be appreciated that the adapter may have a cylindrical extension surrounding the cone 30, the interior surface of which may have female threads for threaded engagement by the flanges 36 of the Luer needle hub 34 to releasably secure the Luer needle to the adapter. To reduce the diameter of the barrel end and also to reduce or eliminate a cylindrical extension of the barrel axially beyond the threads 28, the internal threads of such cylindrical extension may be omitted and a universal Luer connection of the present invention may be provided, either functioning as a Luer fit or Luer lock. To accomplish this, a pair of Luer needle mounting locking elements 100 are provided about the cone 30 on the adapter 24. Particularly, the elements 100 include diametrically opposed axial extending legs 102 terminating in generally circumferentially extending arcuate flanges 104. The flanges 104 are spaced radially outwardly from the cone 30. The tip of each flange 104 is spaced from the axial leg 102 of the adjacent element 100 a distance in excess of the circumferential extent of the conventional flanges 36 on the conventional Luer needle 32. Both upper and lower surfaces of the flanges 104 facing the male threads of the adapter are inclined as in a screwthread.

When the Luer needle is disposed on the cone 30, the Luer needle may form a friction fit, i.e., a Luer fit with the cone 30. That is, when the hub 34 of the Luer needle 32 is placed about the cone 30, the flanges 36 may be oriented to lie between the tips of the flanges 104 and the legs 102 of the adjacent element 100 whereby a complete friction fit of the Luer needle on the cone is effected. If a Luer lock is desired, the hub of the Luer needle may be placed on the cone, as previously described, and then rotated such that the flanges 36 of the Luer needle engage the inclined surfaces of the flanges 104. The Luer needle and adapter flanges 36 and 104, respectively, cooperate to provide a threading action such that the Luer needle hub, upon rotation relative to the adapter, is tightened onto the cone 30.

In a further aspect of the present invention, the Luer needle may be modified to facilitate the removal of the Luer needle when forming a Luer lock with the adapter cone. To that end, a further pair of ribs or flanges 106 (FIG. 6) are provided along the outer surface of the hub 34 in spaced axial alignment with the flanges 36 of the hub. Thus, the adapter flanges 104 may be received between the flanges 106 and 36 on the needle hub when the Luer needle is rotated on the adapter. The lower (outer) surface of the flanges 104 of the adapter are similarly inclined as in a screw thread. Consequently, when the Luer needle is applied as a Luer lock to the adapter, the additional flanges 106 engage along the outer sides of the flanges 104. When the Luer needle is to be removed from the locked position, the rotation of the needle hub and the engagement of the flanges 106 against the outer surfaces of the flanges 104 essentially axially displace the needle hub from the cone 30 of the adapter by an unscrewing action.

Figures 9, 10:
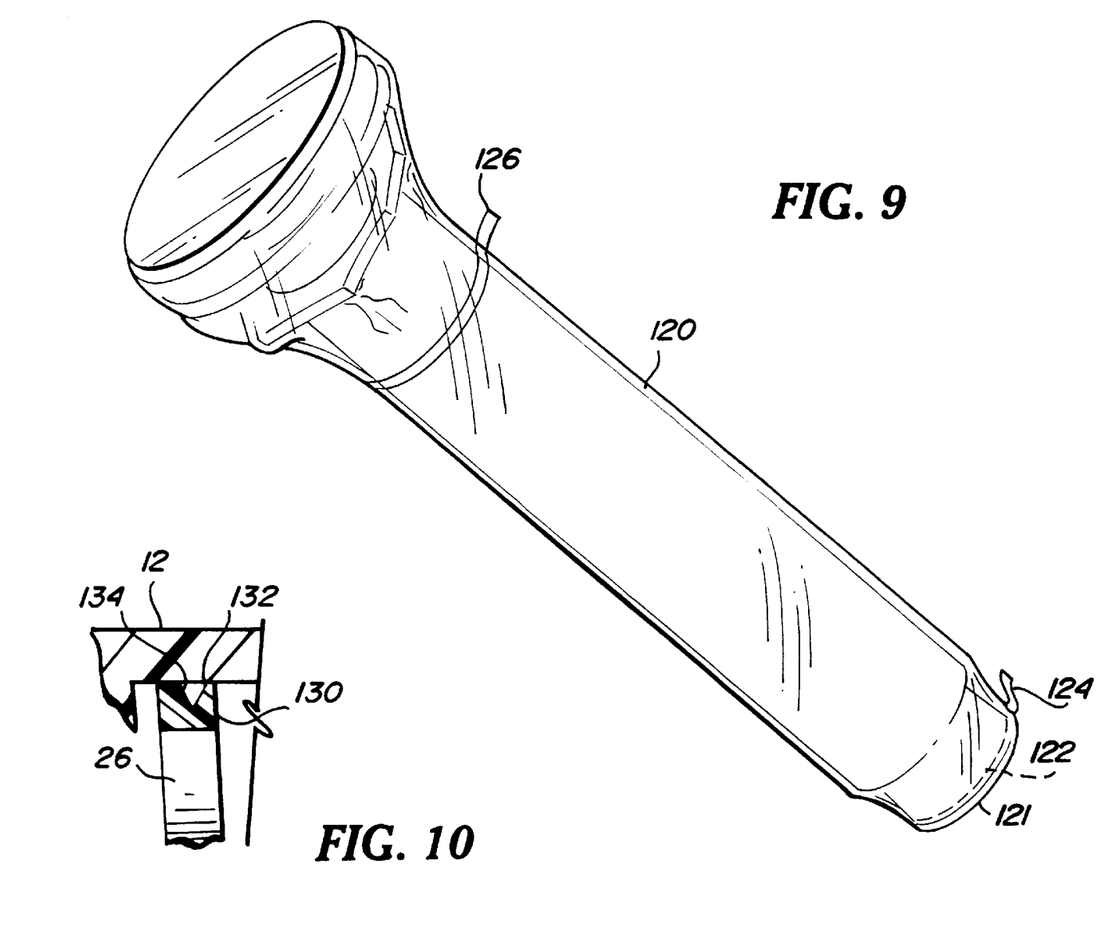
FIG. 9 is a perspective view of a syringe having a shrink-wrapped plastic material about the syringe with tear-off tabs to maintain the syringe in a sterile condition.
FIG. 10 is an enlarged fragmentary cross-sectional view illustrating a seal between the adapter and interior wall of the barrel.

In FIG. 9, the syringe of the present invention without any needle is illustrated in a form in which it would be supplied to a distributor or user. In order to provide a tamper-proof, as well as a sterile syringe, a thin film of plastic material 120 may be provided about the entirety of the syringe. The thin film may take the form of a molten or heat-shrunk plastic material such as described and illustrated in assignee's prior U.S. Pat. No. 5,688,240 and antecedent patents. By applying a shrink-wrapped plastic material, the syringe may be maintained sterile. Any displacement of the plunger relative to the barrel or application of a needle to the adapter projecting from the end of the barrel would be detectable by the disruption in the plastic material. A weakened material may be provided at the distal end of the barrel in the form of a very thin layer of the plastic material. This can be accomplished by a double-molding technique. For example, after the barrel is formed, a second core may be inserted into the barrel extending a plastic wrap material thickness short of the barrel end. A third mold cone covers the end of the barrel. Plastic wrap material is then injected into the space between the second and third cores to form a very thin covering at the barrel end which may have a projecting tab to permit the covering to be readily and easily torn from the syringe. A lip or inherent tab 124 is provided on the removable portion of the plastic cover 121 overlying the distal end of the barrel. When the syringe is ready for use, the user grasps the lip or tab 124 and removes the end cover 121 of plastic material from the barrel end along the weakened portions 122. The user may then also retract the plunger, breaking the shrink-wrap between the finger press and the barrel by means of a second pull tab. It will be appreciated that weakened portions may be provided at that area as well to facilitate disruption of the wrapping prior to withdrawal of the plunger relative to the barrel prior to use. Thus, the user need not unwrap the plastic material from about the syringe to enable the syringe for use.

Alternatively, to allow removal of the shrink wrap at both ends, a small tab may be inserted in the shrink wrap which, when pulled, would separate the shrink wrap into three parts, one very small part at the front which would be removed, a large body part with the tab extending along one side of the barrel from distal to proximal ends and a third smaller component at the junction between the plunger and barrel. Thus, by pulling the single tab which extends the length of the syringe, the entire plastic shrink wrap covering can be removed. Alternatively, as illustrated in FIG. 9, a second tab or strip 126 of plastic material may be formed integrally with the shrink wrap 120 at the proximal end of the barrel. By pulling and removing tab 126, the portion of the wrap about the finger press may be removed, freeing the plunger for movement relative to the barrel and without removal of the central portion of the wrap between the proximal and distal ends of the barrel.

As illustrated in FIG. 10, a seal may be provided between the adapter and the interior wall surface of the barrel. While the screwthreaded connection between the adapter and the barrel has been demonstrated to form an effective seal, a further seal may be desirable. Such seal can be located anywhere along the wall of the adapter and the interior of the barrel. For example, in the form of the seal illustrated in FIG. 10, the seal 130 is formed about the peripheral edge of the disk 26. The seal may take many different forms and shapes and may comprise, for example, an O-ring or a square seal and be formed of such various materials such as rubber. Preferably, however, the seal may be double-molded of plastic materials with the molding of the adapter. In a preferred form, the double-molded seal is formed of a plastic material having a generally V-shaped configuration in cross-section. Alternatively, the seal may comprise an annular seal square in cross-section and having an external V-shaped groove formed in the outer peripheral surface. By double-molding the seal onto the adapter, the necessity of a further part, as well as the complexity and expense of assembling the part into the syringe is avoided. By providing a V-shaped groove or V-shaped configuration of the seal, the seal per se reacts to positive and negative pressures within the syringe barrel. That is, when the syringe barrel is placed under positive pressure by driving the plunger toward the adapter, the leg 132 of the V-shaped seal closest to the plunger bears more firmly against the interior wall of the barrel, enhancing the sealing capacity as a function of increasing positive pressure. Conversely, if the interior of the barrel is subjected to negative pressure, for example, by withdrawing the plunger relative to the adapter, the leg 134 of the V-shaped seal closest to the needle will bear more firmly against the interior wall of the barrel, enhancing its sealing capability as a function of increasing negative pressure.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A universal Luer coupling comprising:

a body having a generally frustoconical male part having an axis and a first diameter and a second diameter smaller than said first diameter and axially spaced from said first diameter, said body terminating in an end adjacent said second diameter, said body having a pair of locking elements spaced radially from said male part and having inclined surfaces facing generally away from said second diameter and toward said first diameter;

a female hub having an axis and an opening through one end of the hub for receiving said male part, said hub including a pair of flanges about said hub projecting outwardly therefrom at generally diametrically opposed sides of said hub, said hub being receivable about said male part with the smaller diameter of said male part disposed within said hub and the axes of said male part and said hub lying generally coincident with one another;

said locking elements comprising a pair of substantially diametrically opposed, axially extending legs terminating in generally circumferentially extending flanges carrying said inclined surfaces, each flange of each said locking element having a distal end, the distal end of each flange of said locking element being spaced circumferentially from an adjacent axial extending leg of another of said locking elements a distance enabling a hub flange to pass therebetween upon said hub being receivable about said male part;

said hub flanges engaging along said inclined surfaces and, in response to relative rotation of said hub and said male part in a first direction, causing said hub to advance toward said large diameter of said male part thereby to tightly engage said hub and said male part to one another.

2. A coupling according to claim 1 wherein said hub carries a needle projecting from an end thereof opposite said open end, said needle having a passageway, said male part having a passage in communication with said passageway in said hub.

3. A coupling according to claim 1 including a second pair of flanges on said hub spaced axially from said first pair thereof and generally axially aligned with said first pair of flanges, a second pair of inclined surfaces carried by said body, said second pair of hub flanges engaging said second pair of inclined surfaces when said hub is received on said male part and said hub and said male part are relatively rotated, said second pair of flanges and said second pair of inclined surfaces being cooperable to displace said hub away from said male part in response to relative rotation of said hub and said male part in a second direction opposite said first direction.

4. A coupling according to claim 1 wherein the distal end of each flange of said locking element is spaced circumferentially from an adjacent axial extending leg of another of said locking elements a distance greater than the circumferential extent of said hub flanges.

5. A universal Luer coupling comprising:

a body having a generally frustoconical male part having an axis and a first diameter and a second diameter smaller than said first diameter and axially spaced from said first diameter, said body terminating in an end adjacent said second diameter, said body having a pair of locking elements spaced radially from said male part and having inclined surfaces facing generally away from said second diameter and toward said first diameter;

a female hub having an axis and an opening through one end of the hub for receiving said male part, said hub including a pair of flanges about said hub projecting outwardly therefrom at generally diametrically opposed sides of said hub;

said locking elements on said male part being spaced circumferentially from one another about said male part a distance sufficient to enable said hub to move axially between said locking elements when said hub is received about said male part with the smaller diameter of said male part disposed within said hub and the axes of said hub and said male part lying generally coincident with one another, thereby affording either a locking fit securing said hub and said male part to one another upon relative rotation of said hub and said male part to engage said hub flanges along said inclined surfaces, or a friction fit securing said male part and said hub to one another;

said locking elements comprising a pair of substantially diametrically opposed, axially extending legs terminating in generally circumferentially extending flanges carrying said inclined surfaces, the distal end of each flange of said locking element being spaced circumferentially from the axial extending leg of another of said locking elements a distance enabling a hub flange to Pass therebetween upon said hub being received about said male part.

6. A coupling according to claim 5, wherein said hub carries a needle projecting from an end thereof opposite said open end, said needle having a passageway, said male part having a passage in communication with said passageway in said hub.

7. A universal Luer coupling for making engagement with a female coupling having a hub with an opening and a pair of flanges about the hub projecting outwardly therefrom at generally diametrically opposed sides of the hub comprising:

a body having a generally frustoconical male part having an axis and a first diameter and a second diameter smaller than said first diameter and axially spaced from said first diameter, said body terminating in an end adjacent said second diameter, said body having a pair of locking elements spaced radially from said male part and having inclined surfaces facing generally away from said second diameter and towards said first diameter, said locking elements comprising a pair of substantially diametrically opposed axially extending legs terminating in generally circumferentially extending flanges carrying said inclined surfaces, each flange of each locking element having a distal end, the distal end of each flange of said locking element being spaced circumferentially from the axial extending leg of another of said locking elements a distance greater than the circumferential extent of the hub flanges of the female hub to enable the hub flanges to be received between the locking elements upon mating engagement of said male part and the female hub.

* * * * *